(12) United States Patent
Verges et al.

(10) Patent No.: US 11,179,599 B2
(45) Date of Patent: Nov. 23, 2021

(54) DEVICE FOR ACCLIMATISING AT ALTITUDE AND METHOD FOR FUNCTIONING THIS DEVICE

(71) Applicants: UNIVERSITE GRENOBLE ALPES, Saint Martin D'Heres (FR); CENTRE HOSPITALIER UNIVERSITAIRE DE GRENOBLE, La Tronche (FR); INSERM (INSTITUT NATIONAL DE LA SANTÉ ET DE LA RECHERCHE MÉDICALE, Paris (FR); UNIVERSITE DE CHAMBERY-UNIVERSITE SAVOIE MONT BLANC, Chambery (FR)

(72) Inventors: Samuel Verges, Eybens (FR); Bernard Wuyam, Echirolles (FR); Thomas Rupp, Chambery (FR)

(73) Assignees: UNIVERSITE GRENOBLE ALPES, Saint Martin d'Heres (FR); CENTRE HOSPITALIER UNIVERSITAIRE DE GRENOBLE, La Tronche (FR); INSERM (INSTITUT NATIONAL DE LA SANTE ET DE LA RECHERCHE MÉDICALE, Paris (FR); UNIVERSITE DE CHAMBERY-UNIVERSITE SAVOIE MONT BLANC, Chambery (FR)

( * ) Notice: Subject to any disclaimer, the term of this patent is extended or adjusted under 35 U.S.C. 154(b) by 410 days.

(21) Appl. No.: 16/072,669

(22) PCT Filed: Jan. 24, 2017

(86) PCT No.: PCT/FR2017/050138
§ 371 (c)(1),
(2) Date: Jul. 25, 2018

(87) PCT Pub. No.: WO2017/129886
PCT Pub. Date: Aug. 3, 2017

(65) Prior Publication Data
US 2019/0060707 A1   Feb. 28, 2019

(30) Foreign Application Priority Data

Jan. 25, 2016 (FR) ...................................... 1650554

(51) Int. Cl.
*A63B 23/18* (2006.01)
*A63B 71/06* (2006.01)
(Continued)

(52) U.S. Cl.
CPC ........... *A63B 23/185* (2013.01); *A61M 16/06* (2013.01); *A61M 16/208* (2013.01);
(Continued)

(58) Field of Classification Search
CPC ........ A63B 23/18–185; A63B 24/0062; A63B 71/0622; A63B 71/0625; A63B 71/063;
(Continued)

(56) References Cited

U.S. PATENT DOCUMENTS

2016/0346603 A1* 12/2016 Halliday ............. A61M 16/208
2017/0333749 A1* 11/2017 McKeown ........... A61B 5/6803

FOREIGN PATENT DOCUMENTS

CN       105126313 A   12/2015
EP       0771578       5/1997
(Continued)

OTHER PUBLICATIONS

Nespoulet et al., Positive Expiratory Pressure Improves Oxygenation in Healthy Subjects Exposed to Hypoxia, Dec. 2013, PLOS ONE, vol. 8, Issue 12, e85219, p. 1-11 (Year: 2013).*
(Continued)

*Primary Examiner* — Elliot S Ruddie
(74) *Attorney, Agent, or Firm* — Hauptman Ham, LLP (57) ABSTRACT

A device for acclimatising at altitude comprising a breathing mask defining a confined air space when it is placed on the face of a user. The mask comprising a suction valve to let the
(Continued)

surrounding air enter inside the confined space when breathing in; an expiration valve to let air exit with a determined resistance, so as to create an overpressurisation of air in the confined space, when breathing out; and a sensor to establish information about the pressure of the confined space behind. The acclimatisation device in addition comprises a unit for processing the pressure information configured to establish a breathing characteristic of the user and compare it to at least one target value, in view of recommending to them an adjustment of the breathing mode thereof. A method for functioning this device is also provided.

8 Claims, 4 Drawing Sheets

(51) Int. Cl.
| | |
|---|---|
| *A63B 24/00* | (2006.01) |
| *A61M 16/06* | (2006.01) |
| *A61M 16/20* | (2006.01) |
| *A63B 21/008* | (2006.01) |
| *A61M 16/00* | (2006.01) |
| *A61M 16/08* | (2006.01) |

(52) U.S. Cl.
CPC .......... *A63B 21/0085* (2013.01); *A63B 23/18* (2013.01); *A63B 24/0062* (2013.01); *A63B 71/0622* (2013.01); *A61M 16/0866* (2014.02); *A61M 2016/0027* (2013.01); *A61M 2205/581* (2013.01); *A61M 2205/582* (2013.01); *A61M 2205/583* (2013.01); *A61M 2230/205* (2013.01); *A63B 21/0088* (2013.01); *A63B 2024/0068* (2013.01); *A63B 2071/063* (2013.01); *A63B 2071/0625* (2013.01); *A63B 2220/56* (2013.01); *A63B 2225/50* (2013.01); *A63B 2225/74* (2020.08); *A63B 2230/405* (2013.01); *A63B 2230/425* (2013.01); *A63B 2230/431* (2013.01)

(58) Field of Classification Search
CPC ......... A63B 21/0085–0088; A63B 2024/0068; A63B 2071/0625; A63B 2071/063; A63B 2207/02; A63B 2220/56; A63B 2225/50; A63B 2230/40–431; A61M 16/06; A61M 16/20–205; A61M 16/208–209; A61M 16/0866; A61M 2016/0027; A61M 2205/581–583; A61M 2230/205; A62B 18/00–04; A61B 5/08; A61B 5/0803; A61B 5/087–0871; A61B 5/1455
USPC ....................................... 607/77–78; 600/538
See application file for complete search history.

(56) References Cited

FOREIGN PATENT DOCUMENTS

| | | |
|---|---|---|
| EP | 3141289 A1 | 3/2017 |
| WO | WO 2015/104522 | 7/2015 |
| WO | WO 2015/120435 | 8/2015 |
| WO | 2015171097 A1 | 11/2015 |

OTHER PUBLICATIONS

International Search Report dated Apr. 25, 2017 with English translation from corresponding application No. PCT/FR2017/050138.

Nespoulet et al., Hugo, "Positive Expiratory Pressure Improves Oxygenation in Healthy Subjects Exposed to Hypoxia," PLOS ONE, www.plosone.org, vol. 8, Issue 12, Dec. 2013, pp. 1-11.

* cited by examiner

FIG. 5

DEVICE FOR ACCLIMATISING AT ALTITUDE AND METHOD FOR FUNCTIONING THIS DEVICE

RELATED APPLICATIONS

The present application is a National Phase of International Application Number PCT/FR2017/050138, filed Jan. 24, 2017, and claims the priority of French Application No. 1650554, filed Jan. 25, 2016.

FIELD OF THE INVENTION

The invention relates to a device for acclimatising at altitude and a method for using this device.

TECHNOLOGICAL BACKGROUND OF THE INVENTION

Altitude involves a lesser availability of oxygen in air breathed and a lesser oxygenation of the body. This hypoxia is well known to be the cause of a decrease in physical and/or cognitive functional capacities and, in certain cases, in the development of headaches, nausea and fatigue.

In the document, "Positive Expiratory Pressure Improves Oxygenation in Healthy Subjects Exposed to Hypoxia" by H. Nespoulet et al (published in the journal "PLOS one" of December 2013, Vol 8, issue 12), it has been shown that adding an expiratory pressure using a ventilation mask on the mouth of a subject in an altitude condition would enable, thanks to the artificial increase in intrapulmonary pressure, to limit the effects of altitude by increasing blood and muscular oxygenation. Such a mask is, for example, defined in document EP0771578.

Although having enabled to validate initial scientific theories, the experimental device used as part of the study reported by the cited document, is not adapted to a current use. Further to the complex configuration thereof, it also requires supervision by specialists, in order to ensure it is used conformingly, and to ensure the effectiveness thereof.

AIM OF THE INVENTION

An aim of the invention is to propose a device for acclimatising at altitude which is compact and easily useable based on simple instructions, enabling to effectively increase the oxygen supply to the body of the user thereof.

BRIEF DESCRIPTION OF THE INVENTION

In view of achieving this aim, the aim of the invention proposes a device for acclimatising at altitude comprising a breathing mask defining a confined air space when it is placed on the face of a user, the mask comprising:
  A suction valve to let surrounding air enter inside the confined space when breathing in;
  An expiration valve to let air exit with a determined resistance, so as to create an overpressurisation of air in the confined space, when breathing out;
  A sensor to establish information about the pressure of the confined air space.

The acclimatisation device in addition comprises a unit for processing pressure information, configured to establish the breathing characteristics of the user and compare them, respectively, to at least one target value, in view of recommending an adjustment of the breathing mode thereof to them, the breathing characteristics comprise the maximum pressure in the confined space when breathing out of a target value of between 8 and 12 cmH2O, the duration of breathing out of a target value of between 3.5 and 4.5 seconds, and the duration of breathing in of a target value 1.5 and 2.5 seconds.

Thus, the user of the device receives instructions enabling them to conformingly use the breathing mask to effectively increase the oxygen supply to the body of the user thereof.

According to other advantageous and non-limiting characteristics of the invention, taken by themselves or in combination:
  The acclimatisation device also comprises a oximeter connected to the processing unit.
  The acclimatisation device also comprises a recommendation unit connected to the processing device.
  The processing unit is arranged in or on the mask.
  The processing unit is arranged or is constituted by a device separate from the mask.

The second aim of the invention is a method for functioning a device for acclimatising at altitude comprising a breathing mask defining a confined air space when it is placed on the face of a user, the method comprising the following steps:
  measuring the pressure of the confined air space;
  establishing, from the pressure measurement, the breathing characteristics of the user;
  comparing the breathing characteristics to at least one target value;
  recommending an adjustment of the breathing mode of the user.

According to the invention, the breathing characteristics are a maximum pressure in the confined space when breathing out of a target value of between 8 and 12 cmH2O, the duration of breathing out of a target value of between 3.5 and 4.5 seconds, and the duration of breathing in of a target value of between 1.5 and 2.5 seconds.

According to other advantageous and non-limiting characteristics of the invention, taken by themselves or in combination:
  the method comprising the illumination of at least one indicator light or the emission of a sound or of a vocal message, or the displaying of a text or a graphic on a screen.
  the method also comprises the recording of the pressure measured and/or the breathing characteristic.

BRIEF DESCRIPTION OF THE DRAWINGS

The invention will be best understood in light of the description which follows, of the specific and non-limiting embodiments of the invention in reference to the appended figures, among which.

DETAILED DESCRIPTION OF THE INVENTION

Very generally, the device for acclimatising to altitude 1 that conforms with the invention comprises a breathing mask 2 to be placed on the face of a user, and a processing unit 3 configured to establish a breathing characteristic of this user, in view of recommending an adjustment to them of the breathing mode thereof.

In the scope of the present application, "breathing characteristic" means any information measured or calculated relating to the air breathed in/out by the user. It can relate to, for example, the quantity of air breathed in or breathed out, the pressure of this air in the mask 2, the time of breathing in and/or breathing out, the breathing rate (in other words, the number of times breathing in/breathing out per time unit). The combination of the breathing characteristics of a user forms, according to the present application, the breathing mode thereof. An adjustment of the breathing mode can therefore correspond to the modification of one or of a plurality of characteristics.

Figure 1:
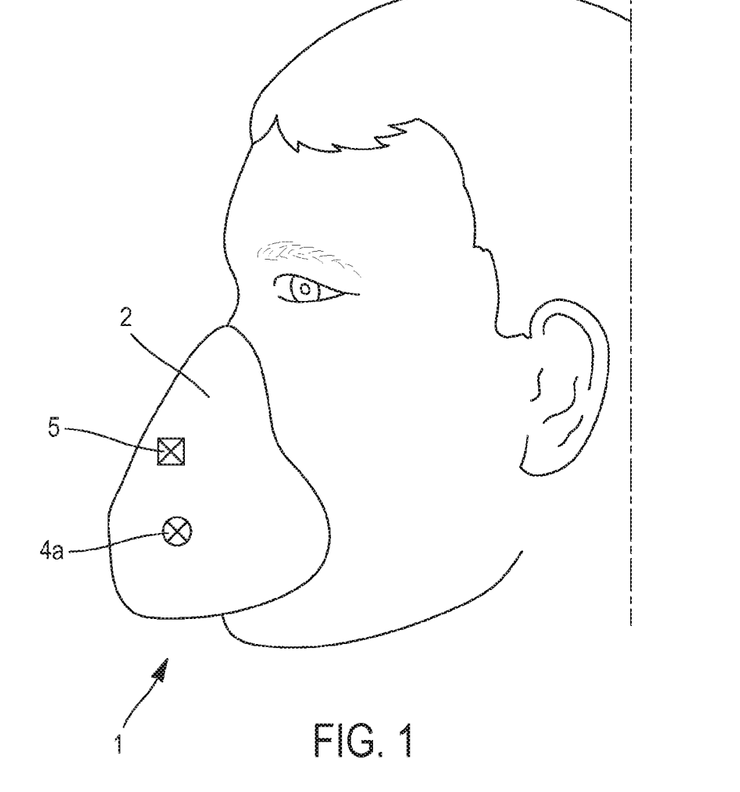
FIG. 1 represents a breathing mask of a device for acclimatising to altitude that conforms with the invention.
Figure 2:
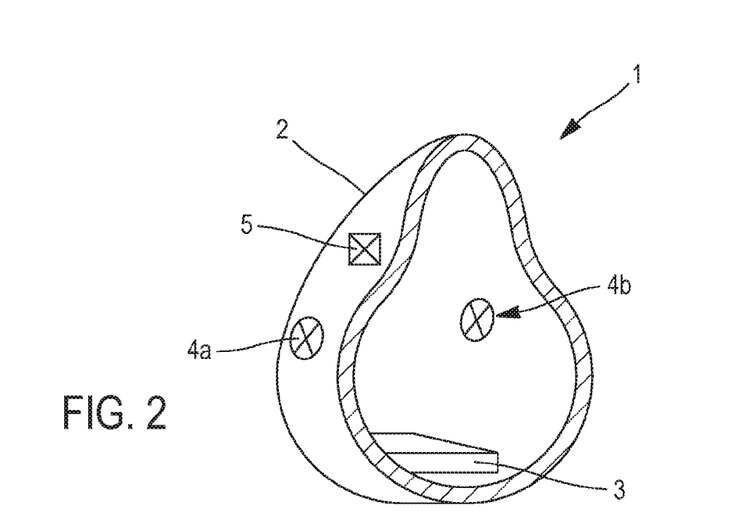
FIG. 2 represents a perspective view of the breathing mask in FIG. 1.

FIG. 1 represents a breathing mask 2 of a device for acclimatising to altitude placed on the face of a user. FIG. 2 represents a perspective view of the mask 2. As is visible in FIG. 1, the mask 2 is configured to surround the mouth and the nose of the user. And as will subsequently be detailed in more detail, it has orifices to let the air breathed in enter and let the air breathed out exit.

The mask 2 is attached on the face by suitable means, such as straps (not represented in the figures), advantageously adjustable to the morphology of the user. Once the mask 2 is positioned, the edge 2*a* thereof is supported on a peripheral supporting zone of the face of the user. The supporting force is preferably chosen such that the wearing of the mask 2 remains comfortable to the user thereof, while ensuring the sufficient sealing of the mask at the level of the supporting zone. Thus, inside the mask, a confined space delimited by the inner surface of the mask 2 and the face of the user are defined.

By "sufficient sealing", this means the air breathed out or breathed in is not likely to pass between the edge 2*a* of the mask and the peripheral supporting zone under normal conditions of use, even when the user breathes under overpressurised expiratory conditions. Thus, and as an example, the sealing between the peripheral supporting zone and the edge 2*a* of the mask 2 can be maintained for a pressure difference between the confined space and the exterior environment going up to 15 cmH2O (1470 Pa), even 20 cmH2O (1960 Pa).

Advantageously, for the stated reasons of comfort and sealing, the edge 2*a* of the mask can be equipped with a support seal (not represented in FIG. 2).

As has been briefly mentioned, the breathing mask 2 is equipped with a first and a second orifice. According to the invention, the first orifice is equipped with a suction valve 4*a* to let the surrounding air enter inside the confined space when breathing in. The second orifice itself is equipped with an expiration valve 4*b* to let air with a resistance or pressure value with a determined threshold exit when breathing out, so as to create an overpressurisation of air in the confined space of the mask 2.

Thus, the user breathing in created a slight under-pressurising inside the mask 2 leading to the opening of the suction valve 4*a* and to the closing of the expiration valve 4*b*, thus enabling the surrounding air to enter into the confined space freely, before being breathed into the lungs of the user.

Similarly, the user breathing out creates an over-pressurising in the confined space of the mask 2 leading to the closing of the suction valve 4*a*. The expiration valve 4*b* itself only opens when the over-pressurising of the confined space exceeds the determined threshold pressure value.

During the conformed use of the mask 2, a type of overpressurisation in the confined space is formed during the breathing out phase, which strongly favours the opening of the pulmonary alveoli of the user, and enables to increase the oxygen supply to the body during following breathing in phases.

The expiration valve 4*b* can be configured such that the determined resistance corresponds to an overpressurisation of the confined space of around 10 cmH2O (980 Pa). More generally, the determined resistance can be between 5 (490 Pa) and 20 cmH2O (1960 Pa).

Advantageously, the determined resistance of the expiration valve 4*b* is adjustable by the user. As an example, the following can be provided:

an expiration valve 4*b* having a first configuration for which the determined resistance corresponds to a first overpressurisation of the confined space, for example 5 cmH2O (490 Pa; and a second configuration for which the determined resistance corresponds to a second overpressurisation of the confined space greater than the first, for example 10 cmH2O (980 Pa).

In this way, one single breathing device 1 can be proposed, which could be used by users having very different morphologies, and obtain a satisfactory acclimatisation at altitude in any case.

The suction and expiration valves 4*a*, 4*b* are the current devices, well known per se, and are typically formed of mechanical valves reacting to the pressure difference existing on either side of the valve, to open or close a passage.

Other forms of implementation of the valves 4*a*, 4*b* are, of course, considerable in the scope of the present invention to ensure the functions which have just been defined.

According to the invention, the mask 2 is also provided with a sensor 5 to provide information about the pressure of the confined space. It can be placed and attached on the inner surface of the mask to have a direct access to the confined space and to determine the pressure thereof. It can also be placed in a housing formed in a wall of the mask, the housing leading to the confined space in order to enable the measurement thereof and in any other place facilitating this measurement.

Advantageously, the sensor 5 provides pressure information in electrical or digital form, in order to enable the processing thereof by the processing unit 3. This information can be provided continuously or with a sufficient frequency vis-à-vis the trends measured to enable the monitoring thereof of the development. Thus, the frequency of making information available can be between 0.1 Hz and 10 Hz.

The device for acclimatising at altitude 1 according to the invention also comprises a unit for processing 3 the information about the pressure of the confined space provided by the sensor 5. To this end, the sensor 5 and the unit 3 are connected to each other by the intermediary of a connection. This connection can correspond to a single electrical connection, a databus in the case where the information is digital, even a wireless connection, for example according to the Bluetooth™ standard. In the case of such a connection, the sensor 5 is equipped with at least emission means, and the receiving means unit 3.

The processing unit 3 can be attached on the mask 2, for example inside it as is represented in FIG. 2, but the invention is not at all limited to this configuration. Thus, the processing unit 3 can also be attached to the exterior of the mask. These two configurations have the advantage of constituting a compact device 1. In this case, the mask is provided with an energy source, such as a power pack or a battery, enabling to supply the active elements such as the processing unit 3, and the possible peripherals thereof.

Alternatively, the unit 3 can be comprised in a device 8 separate from the mask 2, to which it can be connected by a connection cable or by a wireless connection. The separate device 8 can, for example, be an earpiece or another device which could be held by hand, by the user or kept on the wrist thereof.

The functions carried out by the processing unit 3 can be implemented in various forms. Thus, the unit can be constituted of logic and electronic components, integrated or not, or constituted of a microcontroller structure executing a program recorded in a memory, or of a programmable material structure of the FPGA type.

In the case where the unit 3 is comprised or corresponds to a device 8 separate from the mask 2, it can be advantageous to implement the functions thereof in the form of a program being executed on a pre-existing piece of equipment (telephone, watch, tablet, etc.).

Whatever the embodiment of this unit 3, the information about the pressure of the confined air space in the mask 2 is processed there in view of recommending to the user, an adjustment of the breathing mode thereof. This adjustment aims to improve or accelerate acclimatisation at altitude. This can be measured, for example, by the development of arterial oxygen saturation. A use that conforms with the device 1 according to the invention could lead, on average, and at an altitude of 4500 m, to increase this value by 6% or more, which is significant.

The processing unit therefore has the main function of ensuring a use that conforms with the device. To do this, this unit establishes, from the pressure information, breathing characteristics of the user that it compares with target values to establish a recommendation to adjust the breathing mode thereof. More specifically, the processing unit 3 implements a method which comprises the following steps:
- receiving the measurement of the pressure of a confined air space defined by the mask placed on the face of the user;
- establishing, from the pressure measurement, the breathing characteristics of the user;
- respectively comparing the breathing characteristics with a target value in view of recommendation to the user to adjust the breathing mode thereof.

In the scope of the present application, the term "recommendation" and "recommend" correspond to the use of any technical means enabling to communicate to the user, instructions or information relating to the breathing mode thereof, in particular to adjust it and thus use the acclimatisation device 1 conformingly. Generally, these recommendations to adjust the breathing mode are communicated to the user using a recommendation unit 6, connected to the processing unit 3.

A first breathing characteristic established by the processing unit 3 corresponds to the maximum pressure in the confined space being reached when breathing out. Studies carried out by the inventors of the present application have shown that this characteristic needed to preferably be between 8 and 12 cmH2O (between 784 Pa and 1176 Pa).

If, during the processing thereof, the unit 3 identifies through comparison, that the maximum pressure is less than 8 cmH2O, it will be recommended to the user, to breathe out with more force. If, on the contrary, the unit 3 identifies through comparison, that the maximum pressure is greater than 12 cmH2O, it will be recommended to the user, to breathe out with less force.

Finally, if the unit 3 identifies from these comparisons, that the maximum pressure is truly between 8 and 12 cmH2O, it is thus not necessary to communicate any specific recommendation to the user, if this is only about confirming that this breathing characteristic conforms.

A second breathing characteristic is the duration of breathing out and the target value is between 3.5 seconds and 4.5 seconds. The duration of breathing out can be established by the unit 3 by determining the duration during which the information provided by the sensor 5 corresponds to a pressure greater than the surrounding pressure. The recommendations can thus correspond to a lengthening or to a reduction, as the case may be, of the duration of breathing out.

A third breathing characteristic, arising from the second, is the duration of breathing in. The corresponding target value is between 1.5 and 2.5 seconds. Similarly to the preceding case, the duration of breathing in can be established by the unit 3 by determining the duration for which the information provided by the sensor 5 corresponds to a pressure in the confined space being less than the surrounding pressure. The recommendations can thus correspond to a reduction or a lengthening, as the case may be, of the duration of breathing in.

It will be noted, that natural breathing, without applying expiratory pressure, leads to a duration of breathing out of around 2.5 seconds and duration of breathing in of around 2 seconds. Under these natural breathing conditions, arterial oxygenation of a user at 4300 m altitude estimated by an oxygen-pulsed saturation measurement (and commonly represented by the term SpO2) is typically between 75% and 80%. It is reminded, that the SpO2 measurement can be easily obtained using a pulse oximeter, and that this measurement established in % represents the percentage of oxygenated haemoglobin with respect to the total quantity of haemoglobin in the blood.

The inventors of the present application have established that when the expiratory pressure was controlled between 8 and 12 cmH2O, the expiratory time controlled between 3.5 and 4.5 seconds, and the time of breathing in, between 1.5 and 2.5 seconds, the SpO2 measurement showed a rate greater than 80%, and close to 85%, which really shows the particularly noteworthy effect of this breathing mode on the oxygenation of the blood, and on the acclimatisation of a person at altitude.

Of course, the processing carried out by the unit 3 is not limited to the examples which have been given above. In particular, the mask 2 can comprise, or the user can be equipped, with other sensors which could also contribute to the establishment by the unit 3 of recommendations to adjust the breathing mode. The unit 3 can also be configured to record the data received and/or processed in view of a later utilisation.

Thus, and as an example, the user can be equipped with a heart rate sensor or an oximeter which, as in the case of the sensor 5, can be connected to the processing unit 3 using a wired or wireless connection. The availability of an oximeter (which can be placed on the ear or the finger of the user) has the advantage of being able to access an objective measurement of the acclimatisation at altitude of the user. This measurement can be communicated to them, to confirm to them (or not) the conforming use of the device 1 and inform them of the physiological state thereof of acclimatisation at altitude.

Advantageously, the recommendation unit 6 comprises visual means for communicating instructions to the user. It can be a plurality of indicator lights, possibly of different colours, placed on the mask and visible to the user. Alternatively or complimentarily, it can be a screen held in the hand or kept on the wrist, on which the instruction can be displayed in the form of text or graphics.

Alternatively or complimentarily, the recommendation unit 6 comprises communication sound means. It can be a speaker placed on the mask 2 or an earpiece placed on the user themselves, either communicating with the unit 3. These communications can correspond to a plurality of sounds, each one of these sounds being associated with a specific, pre-established recommendation, but advantageously, these communications are pre-recorded messages.

Example 1

Figure 3:
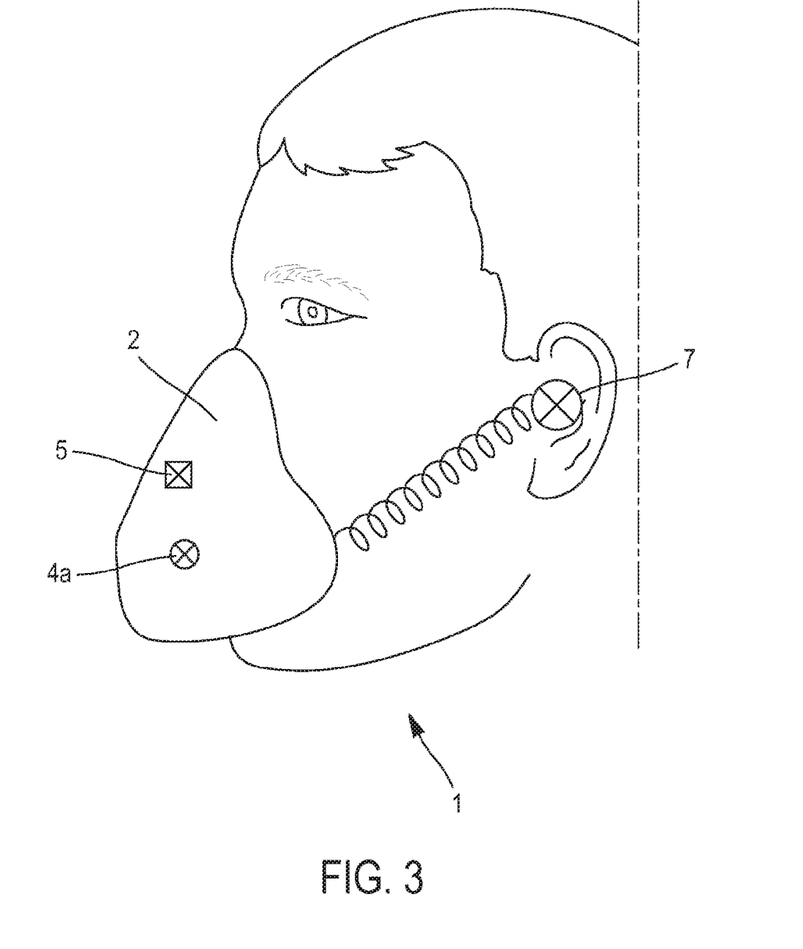
FIGS. 3 to 5 represent specific examples of the device according to the invention.

In FIG. 3, a mask 2 placed on the face of a user is equipped with suction and expiration valves 4a, 4b and a pressure sensor 5 (only the valve 4a is visible in FIG. 3). The processing unit 3 is itself placed inside the mask 2 (and therefore not visible in this figure), in the lower part thereof. This unit is connected to the sensor 5 by a single electrical connection. The unit 3 is also connected to an earpiece 7 (the recommendation unit) placed on the ear of the user, in order to communicate to them in the form of pre-recorded messages, the recommendations to adjust the breathing mode thereof. The unit 3 is, in the case of this example 1, constituted of a microcontroller comprising input/output ports to establish connections with the sensor 5 and the earpiece 7. It also comprises a non-volatile memory wherein resides the processing program, the pre-recorded messages, and wherein can be recorded, the pressure information and the breathing characteristics established during an output for the later utilisation thereof.

Example 2

Figure 4:
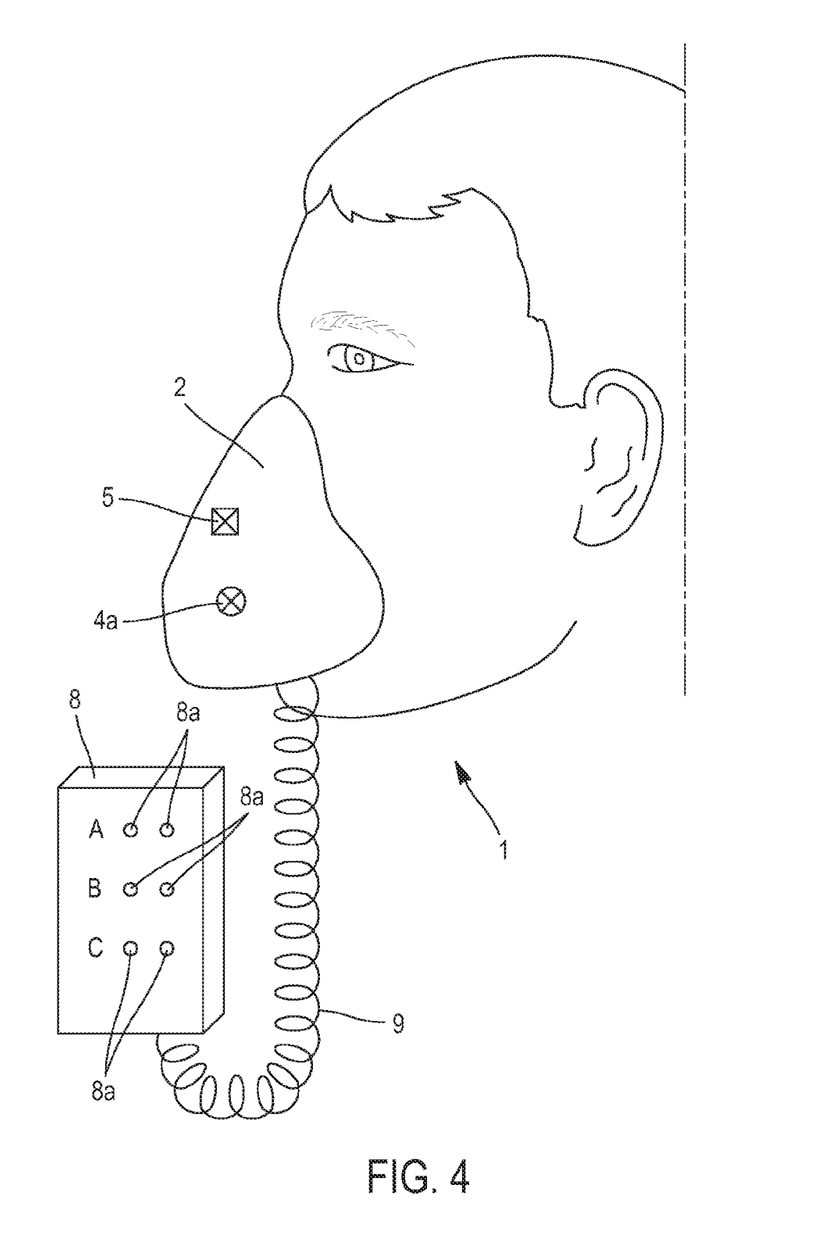

FIG. 4 presents a second example of a device 1 that conforms with the invention. The mask 2 of example 2 is, at any point, similar to that of example 1. However, in this example 2, the recommendations to adjust the breathing mode are communicated to the user using a device 8 separate from the mask 2 and connected to the processing unit 3 by the intermediary of a wired connection 9. The device 8 can be held in the hand or kept on the wrist of the user, for example. It comprises a plurality of indicators lights 8a, each one of these indicators indicating a recommendation, predefined or referring to a predefined characteristic, which can fall into the proximity of the indicator light. In a variant of this example, the wired connection 9 can be replaced by a wireless connection.

Example 3

Figure 5:
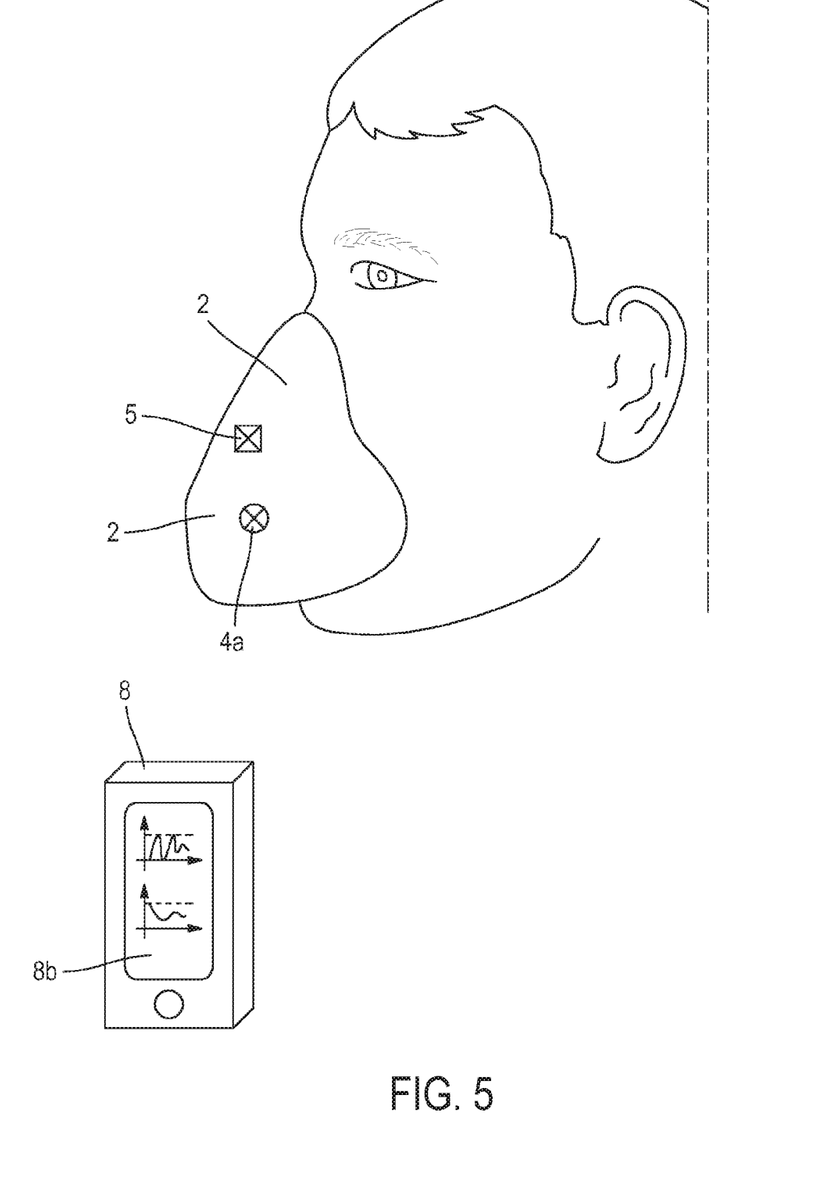

FIG. 5 presents another example of a device 1 that conforms with the invention. In this example, the mask 2 comprises valves 4a, 4b (but only the valve 4a is visible in this figure), and the sensor 5, similar to the mask in the preceding examples. The sensor 5 is equipped with means for communicating information to a separate calculation device 8. Advantageously, the calculation device 8 is a telephone, a tablet, or a smartwatch. An application being executed on these calculation means processes the pressure information received and presents the recommendations to adjust the breathing mode on a display screen 8b, for example in the form of graphics or text.

Of course, the invention is not limited to the embodiments defined and variants of embodiments can be applied without moving away from the scope of the invention such as defined by the claims.

The invention claimed is:

1. An acclimatization device for acclimatizing at altitude, comprising:
a breathing mask defining a confined air space when it is placed on the face of a user, the mask comprising:
a suction valve to let the surrounding air enter inside the confined space when breathing in;
an expiration valve to let the air exit with a determined resistance, so as to create an overpressurisation of air in the confined space, when breathing out;
a sensor to establish pressure information about a pressure of the confined air space; and
a processing unit for processing the pressure information and configured to
establish, from the pressure information, breathing characteristics of the user, and
compare the breathing characteristics of the user, respectively, to at least one target value, to determine an adjustment of a breathing mode of the user,
wherein
the acclimatization device is configured to provide the user with a recommendation of the adjustment of the breathing mode to the user, and
the breathing characteristics include the maximum pressure in the confined space when breathing out of a target value of between 8 and 12 $cmH_2O$, the duration of breathing out of a target value of between 3.5 and 4.5 seconds, and the duration of breathing in of a target value of between 1.5 and 2.5 seconds.

2. The acclimatization device according to claim 1, also comprising an oximeter connected to the processing unit.

3. The acclimatization device according to claim 1, also comprising a recommendation unit connected to the processing unit and configured to provide the user with the recommendation of the adjustment of the breathing mode.

4. The acclimatization device according to claim 1, wherein the processing unit is arranged in or on the mask.

5. The acclimatization device according to claim 1, wherein the processing unit is arranged or is constituted by a device separate from the mask.

6. A method for operating an acclimatization device for acclimatizing at altitude comprising a breathing mask defining a confined air space when the mask is placed on the face of a user, and a processing unit, the method comprising the following steps:
measuring a pressure of the confined air space;
establishing, by the processing unit, from the pressure measurement, breathing characteristics of the user;
comparing, by the processing unit, the breathing characteristics respectively, to at least one target value to determine an adjustment of a breathing mode of the user; and
recommending, by the acclimatization device, the determined adjustment of the breathing mode of the user, and
wherein the breathing characteristics include the maximum pressure in the confined space when breathing out of a target value of between 8 and 12 $cmH_2O$, the duration when breathing out of a target value of between 3.5 and 4.5 seconds, and the duration when breathing in of a target value of between 1.5 and 2.5 seconds.

7. The method for operating the acclimatization device according to claim 6, wherein the recommending step comprises
illumination of at least one indicator light or the emission of a sound or of a vocal message, or
displaying of a text or a graphic on a screen.

8. The method for operating the acclimatization device according to claim 6, wherein the method also comprises recording of the pressure measured and/or the breathing characteristics.

\* \* \* \* \*